United States Patent [19]
Bröker et al.

[11] Patent Number: 5,980,891
[45] Date of Patent: Nov. 9, 1999

[54] SCHIZOSACCHAROMYCES-SPECIFIC POLYPEPTIDES

[76] Inventors: Michael Bröker; Johann Hock, both of Behringwerke Aktiengesellschaft, P. O. Box 1140, D-3550 Marburg, Germany

[21] Appl. No.: 08/345,374

[22] Filed: Nov. 18, 1994

Related U.S. Application Data

[63] Continuation of application No. 08/185,216, Jan. 24, 1994, abandoned, which is a continuation of application No. 07/873,757, Apr. 27, 1992, abandoned.

[30] Foreign Application Priority Data

Apr. 29, 1991 [DE] Germany .................... 41 13 949

[51] Int. Cl.$^6$ ............................ C07K 16/14; C07K 14/39
[52] U.S. Cl. ............................ 424/130.1; 530/388.1; 530/389.1; 530/388.5; 530/371; 530/824; 436/547; 436/548; 435/7.1
[58] Field of Search ........................ 436/547, 548; 530/824, 371, 388.5, 389.1; 433/71

[56] References Cited

U.S. PATENT DOCUMENTS 4,289,690 9/1981 Pestka et al. .

FOREIGN PATENT DOCUMENTS 2011304 9/1990 Canada .

OTHER PUBLICATIONS

Toda et al. Genes and Development 5:60–73, Jan. 1991.
Nagy et al. Eur. J. Biochem 77:77–85, 1977.
Duffus Biochimca et Biophysical Acta 228:627–635, 1971.
Schweingruber et al. J. Biol. Chem. 251(34):15877–882, Dec. 1986.

Harlow and Lane (Ed.), "Antibodies, A Labatory Manual", see pp. 139–141, 283, and 288, 1988.

L. Xiang–Huai et al. Acta Mycologica Sinica 9(1):50–55 1990.

Tomashita et al. Develop. Growth and Differ. 33(6):617–624 1991.

Harlow and Lane. Antibodies a Laboratory Manual. Cold Spring Harbor Laboratory 1988–see pp. 555–592.

Bröker. Identification of the Yeast . . . Current Microbiology vol. 22 1991 pp. 339–343.

Lu et al. Polyacrylamide gelelectrophoresis . . . Zhenjun Xuebao 9(1)50–5 1990 (abstract enclosed).

Kreutzfeldt et al. Immunological Homologies . . . Curr Genet. 1986 10:537–544.

Tortora et al. Microbiology and Introduction—Monoclonal Antibodies pp. 423–424 1989.

Kudla et al., "Construction of an Expression Vector for the Fission Yeast *Schizosaccharomyces pombe*", Nucleic Acids Research, 16: 8603–8617 (1988).

European Search Report, dated Apr. 8, 1993.

*Primary Examiner*—Marianne P. Allen
*Attorney, Agent, or Firm*—Finnegan, Henderson, Farabow, Garrett & Dunner, L.L.P.

[57] ABSTRACT

The invention relates to novel Schizosaccharomyces-specific proteins and their antibodies. These proteins and antibodies can be used for identifying the yeast genus Schizosaccharomyces.

12 Claims, No Drawings

SCHIZOSACCHAROMYCES-SPECIFIC POLYPEPTIDES

This application is a continuation of application Ser. No. 08/185,216, filed Jan. 24, 1994, now abandoned which is a continuation application Ser. No. 07/873,757, Filed Apr. 27, 1992, now abandoned.

The invention relates to novel Schizosaccharomyces-specific proteins and their antibodies. These proteins and antibodies can be used for identifying the yeast genus Schizosaccharomyces.

Slooff (W. C. Slooff (1970) "Genus 19. Schizosaccharomyces" in The Yeast. A taxonomic study. The North Holland Publishing Co. Amsterdam, pp. 733–755) describes the fission yeast Schizosaccharomyces as comprising four species: *S. pombe, S. malidevorans, S. octosporus* and *S. japonicus. S. japonicus*, in turn, is subdivided into *S. japonicus* var. *japonicus* and *S. japonicus* var. *versatilis*. However, this taxonomy is not generally accepted, and the possibility of introducing additional denominations of genera, such as Octosporomyces or Hasegawaea, is being discussed.

Apart from morphological criteria, the identification and classification of yeasts is generally based on physiological properties such as the utilization of mono-, di- and trisaccharides, the utilization of nitrate and the need for certain vitamins. However, identification by virtue of these characteristics is not always unambiguous and can also result in mistakes.

It has now been found that certain proteins which are recognized by the murine monoclonal antibody mAb JHF13-17, are specific for Schizosaccharomyces.

The hybridoma which secretes the abovementioned mAb JHF13-17 was deposited on Mar. 6, 1991 at the Deutsche Sammlung von Mikroorganismen und Zellkulturen G.m.b.H. (DSM) [German Collection of Microorganisms and Cell Cultures G.m.b.H. (DSM) Mascheroder Weg 1B, D-3300, Braunschweig, Germany,] in accordance with the Budapest Treaty and assigned the number DSM ACC 2005.

The invention therefore relates to:
1. Polypeptides, or immunogenic portions thereof, from Schizosaccharomyces, which are recognized by the monoclonal antibody JHF13-17.
2. Monoclonal antibody JHF13-17.
3. Monoclonal or polyclonal antibodies against polypeptides or immunogenic portions from Schizosaccharomyces, in which the polypeptides, or immunogenic portions thereof, are recognized by the monoclonal antibody JHF13-17.
4. Process for the preparation of polyclonal antibodies, wherein
   a) Polypeptides, or immunogenic portions thereof, which are recognized by the monoclonal antibody JHF13-17, are isolated and
   b) a suitable organism is immunized with the polypeptides, or immunogenic portions, from step a).
5. Process for identifying Schizosaccharomyces, wherein Schizosaccharomyces together with antibodies against polypeptides, or immunogenic portions thereof, is incubated as claimed in claim 1.
6. Use of antibody against polypeptides, or immunogenic portions thereof, which are recognized by the monoclonal antibody JHF13-17, for identifying Schizosaccharomyces.
7. Composition for identifying Schizosaccharomyces, which comprises antibodies against polypeptides, or immunogenic portions thereof, which are recognized by the monoclonal antibody JHF13-17.

The invention, in particular in its preferred embodiments, will be described in detail hereinafter. An immunoenzymatic method as is described, for example, by Burnette (Burnette W. N. (1981) Anal. Biochem. 112, 195–203) which used the murine monoclonal antibody mAb JHF13-17, detected two Schizosaccharomyces-specific polypeptides SSP-A and SSP-B in *S. pombe, S. malidevorans* and *S. japonicus*. Using the same mAb, two further Schizosaccharomyces-specific polypeptides SSP-B' and SSP-C were found in *S. octosporus*. However, the polypeptides SSP-A, SSP-B, SSP-B' or SSP-C were not detected in the following yeast species which do not belong to the genus Schizosaccharomyces: *Bullera alba, Candida albicans, Candida krusei, Candida parapsilosis, Candida tropicalis, Cryptococcus neoformans, Cryptococcus terreus, Exobasidium japonicum, Filobasidium floriforme, Hansenula polymorpha, Kluyveromyces lactis, Leucosporidium nivale, Metschnikowia pulcherrima, Rhodotorula graminis, Rhodotorula minuta, Rhodotorula rubra, Saccharomyces cerevisiae, Saccharomycodes ludwigii, Sporobolomyces holsaticus, Trichsporon cutaneum, Trigonopsis variabilis* and *Ustilago zeae*.

The Schizosaccharomyces-specific polypeptides (SSP-A, SSP-B, SSP-B' and SSP-C) were also not detected in, for example, *Escherichia coli* nor in goat and rabbit sera.

The relative molecular weight of the polypeptides found is generally determined by comparison with size standards. A polypeptide according to the present invention is from Schizosaccharomyces, is recognized by the monoclonal antibody JHF13-17 (DSM ACC 2005), and has a relative molecular weight of approximately 40,000–60,000 under denaturing conditions. The bands of proteins SSP-A, SSP-B or SSP-B' and SSP-C were detected in a molecular weight range of approx. 40,000 to 60,000 under denaturing conditions, for example in an SDS polyacrylamide gel. The following relative molecular weights were preferably determined for the individual protein bands:

SSP-A: 50,000–54,000, in particular approx. 52,000

SSP-B or SSP-B': 48,000–52,000, in particular approx. 50,000

SSP-C: 46,000–50,000, in particular approx. 48,000

The invention furthermore relates to polyclonal antibodies against SSP-A, SSP-B, SSP-B' and SSP-C, which can be obtained by known methods, for example by the method of Coghlan L. G. & Hanausek M. (1990), J. Immunol. Meth. 129, 135–138. The monospecific polyclonal antibodies obtained can be used to demonstrate that it is not only an immunogenic portion, or epitope, of the protein in question that is specific for Schizosaccharomyces, but the polypeptides SSP-A, SSP-B, SSP-B' and SSP-C as such. Finally, the invention also embraces mAbs against the abovementioned polypeptides which are functionally different from mAb JH13-17 and, as a consequence, recognize other epitopes of the polypeptides according to the invention. These mAbs are produced by generally known methods, for example by the method of Ed Harlow and David Lane, eds. Antibodies. A Laboratory Manual, Cold Spring Harbor Laboratory, Cold Spring Harbor, N.Y. (1988). The monoclonal or polyclonal antibodies, in particular mAb JH13-17, are generally used for identifying the yeast genus Schizosaccharomyces, for example in immunofluorescence, immunoblotting or in ELISA tests. Apart from monoclonal antibodies, monospecific polyclonal antibodies can furthermore also be used for isolating SSP-A, SSP-B, SSP-B' and/or SSP-C by generally known methods, for example by affinity chromatography.

With the aid of mAb JHF13-17, it is also possible to clone the genes which encode SSP-A, SSP-B, SSP-B' or SSP-C, and to identify Schizosaccharomyces via the specific DNA or RNA sequences. Furthermore, the SSP genes or their coding regions can be transformed into other yeasts, where they act as specific markers.

The detection of Schizosaccharomyces is used, in particular, in quality control, for example in the production of alcohol from molasses, in wine making or in the heterologous production of proteins in Schizosaccharomyces. The specific and sensitive detection of Schizosaccharomyces is a particular advantage. Yeast hybrids as have been produced, for example, between the species *Saccharomyces cerevisiae* and *S. pombe*, can therefore be identified unambiguously.

The invention will be illustrated in greater detail by the following examples:

EXAMPLE 1

A range of microorganisms was cultured for 3 days in YPD medium (1% yeast extract, 2%peptone, 2% glucose) in 250 ml Erlenmeyer flasks in a shaker at 180 rpm at 15° C. and 30° C. 10 ml aliquots of culture liquid were centrifuged, and the cells were then harvested, taken up in 1 ml of 10 mM Tris-$^{buffer}$ (pH 7.5), glass beads were added, and the batch was treated in a glass bead mill. The homogenate was then heated by the method of Laemmli (U. K. Laemmli (1970) Nature 227, 680–685), separated in a 10% strength SDS polyacrylamide gel and transferred to nitrocellulose membranes (Burnette W. N. loc. cit.). The nitrocellulose strips were then incubated in Tris-buffer (10 mM Tris HCl, pH 7.5, 150 mM NaCl, 1% gelatin, 4% TWEEN 20 (Polyethylenesorbiton monolaurate) containing the mAb JHF13-17 (10 μg/ml). Anti-mouse antibodies coupled to alkaline phosphatase were used as conjugate. The substrates used were Fast Blue B salt (O Diansidine) (manufactured by Serva, Heidelberg) and Naphtol AS-MX phosphate (3-Hydroxy-2-naphtoric acid-2,4-dimethylanilide phosphate (manufactured by Sigma Chemie, Munich).

To determine the relative molecular weight, Rainbows™ Protein molecular weight markers (mixture of individual colored proteins of defined molecular weight) (Amersham Buchler GmbH, Brunswick) were additionally applied to the nitrocellulose strips.

Using mAb JHF13-17, Schizosaccharomyces-specific proteins were detected in the following Schizosaccharomyces strains. (List 1).

| Organism | Strain collection |
| --- | --- |
| *S. pombe* | CBS 5680 |
| | CBS 1057 |
| | DSM 3796 (leu, hiS)[a] |
| | CSIR Y-467 |
| | CBS 1043 |
| | CBS 1043 |
| *S. malidevorans* | NCYC 683 |
| | VLSF 0401 |
| | CBS 3557 |
| | BLWG 442 |
| *S. japonicus* var. *japonicus* | |
| | VLSF 03/11 |
| | VLSF 03/201 |
| | IFO 1609 |
| | IFO 1646 |
| | IFO 1712 |
| *S. japonicus* var. *versatilis* | |
| | NCYC 419 |
| | IFO 1607 |
| *S. octosporus* | NCYC 131 |
| | VLSF 0101 |
| | CBS 2631 |
| | CBS 1804 |
| | CBS 2632 |
| | CBS 371 |

-continued

| Organism | Strain collection |
| --- | --- |
| | CBS 6209 |
| | BLWG H80 |
| | ATCC 2479 |

[a] = genetic marker

List of abbreviations of the strain collections:

The Centraalbureau voor Schimmelcultures (CBS), Baarn, The Netherlands; Deutsche Stammsammlung für Mikroorganismen und Zellkulturen GmbH (DSM), Brunswick, Federal Republic of Germany; Versuchs- und Lehranstalt für Spiritusfabrikation und Fermentationstechnologie in Berlin (VLSF), Berlin, Federal Republic of Germany; Institute for Fermentation (IFO), Osaka, Japan; Council of Science of Industrial Research (CSIR), Pretoria, South Africa; National Collection of Yeast Cultures (NCYC), Norwich, England; Bayerische Landesanstalt für Weinbau und Gartenbau (BLWG), Würzburg, Federal Republic of Germany; American Type Culture Collection (ATCC), Rockville, Md., USA.

Cell extracts of *S. pombe*, *S. malidevorans* and *S. japonicus* in each case showed a double band having a relative molecular weight of approx. 52,000 (SSP-A) and approx. 50,000 (SSP-B). The mobility of the double band in electrophoresis was identical in all test strains. It is assumed that the two proteins are related to each other by virtue of their cross-reactivity with mAb JHF13-17.

Cell extracts of *S. octosporus* also showed a double band by the above described method. In contrast, its mobility in electrophoresis differs by the fact that the upper protein band (SSP-B') migrates at the level of SSP-B from *S. pombe*, *S. malidevorans* and *S. japonicus*. The second *S. octosporus* protein (SSP-C) has a relative molecular weight of approx. 48,000. The mobility of the double band in electrophoresis was identical in the *S. octosporus* test strains.

EXAMPLE 2

To answer the question as to whether proteins SSP-A, SSP-B and SSP-C, which react with mAb JHF13-17, are specific for fission yeasts, cell extracts of 23 other yeast species were examined by the method described in Example 1 (List 2). The test species were:
*Bullera alba* DSM 70002
*Candida albicans*
*Candida krusei*
*Candida parapsilosis*
*Candida tropicalis*
*Cryptococcus neoformans*
*Cryptococcus terreus* DSM 70222
*Exobasidium japonicum* DSM 4461
*Filobasidium floriforme* DSM 4655
*Hansenula polymorpha* (leul)[a]
*Kluyveromyces lactis* SD11 (lac4, trp1)[a]
*Leucosporidium nivale* DSM 4635
*Metschnikowia pulcherrima* DSM 70879
*Rhodotorula graminis*
*Rhodotorula minuta*
*Rhodotorula rubra*
*Saccharomyces cerevisiae* VLSF 104
*Saccharomyces cerevisiae* (ura3-2, leu2, his, pra1, prb1, prc1, cps1)[a]
*Saccharomycodes ludwigii* DSM 3447
*Sporobolomyces holsaticus* DSM 70580
*Sterigmatomyces halophilus* DSM 4668

*Trichosporon cutaneum* DSM 70698
*Trichosporon cutaneum*
*Trigonopsis variabilis* DSM 70714
*Ustilago zeae* DSM 4500
*a)*=genetic marker The result was that no protein was specifically detected with mAb JHF13-17 in any of these yeast species. Equally, cell extracts of *Escherichia coli* as well as goat and rabbit serum contained no protein which had been recognized specifically by mAb JHF13-17. The epitope which is recognized by mAb JHF13-17 on the proteins SSP-A, SSP-B, SSP-B' and SSP-C is therefore specific for fission yeasts.

EXAMPLE 3

To demonstrate that not only an epitope of the Schizosaccharomyces-specific proteins (SSPs) which are recognized by the mAb JHF13-17, is specific, but that the protein as such is specific for Schizosaccharomyces, a polyclonal serum against SSP-A and SSP-B was prepared from *S. pombe*. For this purpose, the proteins of an *S. pombe* cell extract was transferred to nitrocellulose by the method described in Example 1, and the section which corresponds to the position of SSP-A and SSP-B was excised. Rabbits were then immunized with these nitrocellulose-bound SSP-A and SSP-B by the method of Coglan and Hanausek (J. Immunol. Method. 129, 135–138 [1990]. In Western blot analyses, the monospecific polyclonal antisera obtained only reacted with the SSPs of the four Schizosaccharomyces species (SSP-A, SSP-B, SSP-B' and SSP-C), but not with other cell extract proteins or with proteins from different yeast species. As a consequence, the abovementioned SSPs are specific for fission yeasts.

What is claimed is:

1. A purified and isolated polypeptide specific to Schizosaccharomyces, comprising an epitope which is recognized by the monoclonal antibody JHF13-17 (DSM ACC 2005) and has a relative molecular weight within the range of approximately 400,000–60,000 under denaturing conditions.

2. The polypeptide as claimed in claim 1, which is purified and isolated from a yeast selected from the group consisting of *S. pombe, S. malidevorans, S. japonicus*, and *S. octosporus*.

3. A monoclonal antibody against a polypeptide as claimed in claim 1.

4. An isolated polyclonal antibody against a polypeptide as claimed in claim 1.

5. A process for identifying Schizosaccharomyces in a sample, comprising a) contacting the sample with an antibody which binds to the polypeptide of claim 1, and b) detecting antibody binding to any Schizosaccharomyes in the sample.

6. The process as claimed in claim 5, wherein the antibody is polyclonal or monoclonal.

7. A polypeptide as claimed in claim 1, wherein said polypeptide is SSP-A which has a relative molecular weight under denaturing conditions of 50,000–54,000, SSP-B or SSP-B' which has a relative molecular weight under denaturing conditions of 48,000–52,000, or SSP-C which has a relative molecular weight under denaturing conditions of 46,000–50,000.

8. A process for the preparation of a polyclonal antibody, which comprises a) isolating a polypeptide, or an antigenic portion therefrom from Schizosaccharomyces, which is recognized by the monoclonal antibody JHF13-17, b) immunizing a suitable organism with a polypeptide, or an antigenic portion thereof, from step a), and c) isolating a polyclonal antibody produced by the immunizing of said organism.

9. A composition for identifying Schizosaccharomyces, wherein said composition comprises:

(a) an antibody against a polypeptide as claimed in claim 1, and (b) a carrier.

10. A purified and isolated polypeptide specific to Schizosaccharomyces, comprising an epitope which is recognized by the monoclonal antibody JHF13-17 (DSM ACC 2005), wherein said polypeptide has a molecular weight within the range of approximately 46,000–54,000 under denaturing condition.

11. Monoclonal antibody JHF13-17.

12. A process for identifying Schizosaccharomyces in a sample, comprising:

a) contacting the sample with monoclonal antibody JHF13-17, and b) detecting antibody binding to any Schizosaccharomyces in the sample.

* * * * *